(12) United States Patent
Schlitter et al.

(10) Patent No.: US 7,307,040 B2
(45) Date of Patent: Dec. 11, 2007

(54) METHOD FOR THE SELECTIVE PRODUCTION OF TETRAHYDROFURAN BY HYDROGENATING MALEIC ACID ANHYDRIDE

(75) Inventors: Stephan Schlitter, Limburgerhof (DE); Holger Borchert, Offstein (DE); Michael Hesse, Worms (DE); Markus Schubert, Ludwigshafen (DE); Nils Bottke, Mannheim (DE); Rolf-Hartmuth Fischer, Heidelberg (DE); Markus Rösch, Oppenheim (DE); Gunnar Heydrich, Limburgerhof (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 368 days.

(21) Appl. No.: 10/482,645

(22) PCT Filed: Jul. 3, 2002

(86) PCT No.: PCT/EP02/07341

§ 371 (c)(1),
(2), (4) Date: Jan. 5, 2004

(87) PCT Pub. No.: WO03/006445

PCT Pub. Date: Jan. 23, 2003

(65) Prior Publication Data
US 2004/0198596 A1 Oct. 7, 2004

(30) Foreign Application Priority Data
Jul. 7, 2001 (DE) .................... 101 33 054

(51) Int. Cl.
*B01J 23/56* (2006.01)
*B01J 23/00* (2006.01)

(52) U.S. Cl. .................... 502/331; 502/332; 502/333; 502/339; 502/346

(58) Field of Classification Search ............. 502/245, 502/331, 333, 339, 345, 346, 415, 439, 349, 502/350, 303, 304
See application file for complete search history.

(56) References Cited

U.S. PATENT DOCUMENTS

| | | | |
|---|---|---|---|
| 1,036,510 A | 8/1912 | Murray | |
| 2,967,835 A * | 1/1961 | Hort | 502/184 |
| 3,065,243 A | 11/1962 | Dunlop et al. | |
| 3,224,981 A * | 12/1965 | Hirschler, Jr. et al. | 502/245 |
| 3,282,861 A * | 11/1966 | Beveridge | 502/245 |
| 3,397,154 A * | 8/1968 | Talsma | 502/304 |
| 3,580,930 A | 5/1971 | Miya et al. | |
| 3,791,991 A * | 2/1974 | Seale et al. | 502/184 |
| 4,006,165 A | 2/1977 | Michalczyk et al. | |
| 4,058,485 A * | 11/1977 | Cheung | 502/331 |
| 4,083,809 A | 4/1978 | DeThomas et al. | |
| 4,101,451 A * | 7/1978 | Frevel et al. | 502/315 |
| 4,105,674 A | 8/1978 | DeThomas et al. | |
| 5,122,495 A | 6/1992 | Taylor et al. | |
| 5,149,836 A | 9/1992 | DeThomas et al. | |
| 5,536,849 A | 7/1996 | Bergfeld et al. | |
| 5,905,056 A * | 5/1999 | Hartweg et al. | 423/213.2 |
| 6,048,820 A * | 4/2000 | Takeuchi et al. | 502/244 |
| 6,355,597 B1 * | 3/2002 | Spivack et al. | 502/353 |
| 6,383,979 B1 * | 5/2002 | McCauley et al. | 502/331 |
| 6,534,432 B1 * | 3/2003 | Spivack et al. | 502/102 |
| 6,576,588 B2 * | 6/2003 | Ryu et al. | 502/331 |
| 6,627,578 B2 * | 9/2003 | Xu et al. | 502/331 |
| 6,685,899 B1 * | 2/2004 | Park | 423/213.5 |
| 6,756,339 B1 * | 6/2004 | Rokicki et al. | 502/304 |
| 6,784,135 B2 * | 8/2004 | Scholten et al. | 502/245 |
| 2001/0016188 A1* | 8/2001 | Haga et al. | 423/648.1 |
| 2002/0131915 A1* | 9/2002 | Shore et al. | 422/177 |

FOREIGN PATENT DOCUMENTS

| | | |
|---|---|---|
| EP | 638 565 | 2/1995 |
| WO | 95/22539 | 8/1995 |
| WO | 99/35139 | 7/1999 |
| WO | 99/38856 | 8/1999 |

* cited by examiner

*Primary Examiner*—Cam N. Nguyen
(74) *Attorney, Agent, or Firm*—Novak Druce & Quigg, LLP

(57) ABSTRACT

A catalyst for the hydrogenation of $C_4$-dicarboxylic acids and/or derivatives thereof, preferably maleic anhydride, in the gas phase comprises a) 20-94% by weight of copper oxide (CuO), preferably 40-92% by weight of CuO, in particular 60-90% by weight of CuO, and b) 0.005-5% by weight, preferably 0.01-3% by weight, in particular 0.05-2% by weight, palladium and/or a palladium compound (calculated as metallic palladium) and c) 2-79.995% by weight, preferably 5-59.99% by weight, in particular 8-39.95% by weight, of an oxidic support selected from the group consisting of the oxides of Al, Si, Zn, La, Ce, the elements of groups IIIA to VIIIA and of groups IA and IIA of the Periodic Table of the Elements.

4 Claims, No Drawings

METHOD FOR THE SELECTIVE PRODUCTION OF TETRAHYDROFURAN BY HYDROGENATING MALEIC ACID ANHYDRIDE

The present invention relates to a process for preparing unsubstituted or alkyl-substituted γ-butyrolactone and tetrahydrofuran by catalytic hydrogenation in the gas phase of substrates selected from the group consisting of maleic acid and succinic acid and derivatives of these acids. For the purposes of the present invention, these derivatives are esters and anhydrides which, like the acids, may bear one or more alkyl substituents. The catalyst used is an all-active catalyst (i.e. a catalyst having the same composition throughout, as distinct from a coated catalyst) comprising copper oxide, palladium and/or a palladium compound and at least one further metal oxide.

The preparation of γ-butyrolactone (GBL) and tetrahydrofuran (THF) by gas-phase hydrogenation of maleic anhydride (MA) is a reaction which has been known for many years. Numerous catalyst systems for carrying out this catalytic reaction are described in the literature. These are mostly Cr-containing. Depending on the composition of the catalyst and the reaction parameters chosen, different product distributions are achieved using such catalysts.

Apart from MA, further possible starting materials for preparing GBL and THF are maleic acid itself, succinic acid and its anhydride and the esters of these acids. If alkyl-substituted GBL and THF are to be prepared, it is possible to use the correspondingly alkyl-substituted species derived from the abovementioned acids, esters and anhydrides.

U.S. Pat. No. 3,065,243 discloses a process in which copper chromite serves as catalyst. According to the description and examples, appreciable amounts of succinic anhydride (SA) are formed in this process and have to be circulated. As is known, this frequently results in process engineering problems caused by crystallization of the SA or succinic acid formed therefrom with subsequent blockage of pipes.

Further copper chromite catalysts for the hydrogenation of MA are disclosed, for example, in U.S. Pat. No. 3,580,930, U.S. Pat. No. 4,006,165, EP-A 638 565 and WO 99/38856. According to these disclosures, high yields of GBL can be achieved using the catalysts described there. THF is in each case formed only in traces. However, it is often the case that relatively large amounts of THF are desired for a number of reasons.

A process which allows this is disclosed in U.S. Pat. No. 5,072,009. The catalysts used according to this patent have the formula $Cu_1Zn_bAl_cM_dO_x$, where M is at least one element selected from the group consisting of groups IIA and IIIA, VA, VIII, Ag, Au, the groups IIIB to VIIB and the lanthanides and actinides of the Periodic Table of the Elements, b is from 0.001 to 500, c is from 0.001 to 500 and d is from 0 to <200 and x corresponds to the number of oxygen atoms necessary to meet the valence criteria. Although it is stated that no chromium needs to be present in the catalysts disclosed in this patent, chromium-containing catalysts are described in all examples. According to these examples, a maximum THF yield of 96% is obtained, and the hydrogenation is carried out at pressures of from 20 to 40 bar.

A two-stage catalyst system for the hydrogenation of MA is described in U.S. Pat. No. 5,149,836. The catalyst for the first stage is free of chromium while the catalyst for the second stage is based on Cu—Zn—Cr oxides.

An in-principle disadvantage of all the above-described catalyst systems is the presence of chromium oxide, whose use should be avoided because of its acute toxicity. Such Cr-free catalyst systems for preparing GBL by hydrogenation of MA have also been described in the prior art. Examples of such catalyst systems may be found in WO 99/35139 (Cu—Zn oxide), WO 95/22539 (Cu—Zn—Zr) and U.S. Pat. No. 5,122,495 (Cu—Zn—Al oxide). All these catalyst systems make it possible to obtain high yields of GBL, up to 98%, but THF is formed only in traces, if at all. Although the formation of THF can, as is known, be promoted by an increase in the reaction temperature or relatively long residence times in the reactor, the proportion of undesirable by-products, for example butanol, butane, ethanol or ethane, increases at the same time.

A catalyst for the gas-phase hydrogenation of MA to GBL which is made up exclusively of Cu and Al oxides is disclosed in Wo 97/24346. This, too, suffers from the same disadvantages as the processes disclosed in the documents described in the previous paragraph, namely only minor formation of THF which can be increased only by means of extreme reaction conditions.

The use of a catalyst having in principle the same composition as that described in WO 97/24346, namely based on Cu—Al oxides, is also disclosed in JP 2 233 631. The aim of this invention is to carry out the hydrogenation of MA in such a way that THF and 1,4-butanediol are formed as main products together with only small amounts, if any, of GBL. This is achieved by the use of the catalysts based on mixed Cu—Al oxides and by adherence to particular reaction conditions. Typical mixtures obtained using this process comprise from about 15 to 20 mol % of 1,4-butanediol and from 60 to 80 mol % of THF, with the amount of THF even being able to be increased to above 99 mol % according to one example. This is achieved by using a large excess of GBL as solvent. In contrast, if no solvent is employed, the yields drop considerably to values in the region of 75%.

U.S. Pat. No. 4,105,674 discloses a process for the hydrogenation of maleic acid, succinic acid or their anhydrides over supported or unsupported Cu—Pd or Cu—Pt catalysts. The aim of that invention is to produce GBL in high yields and with formation of very small amounts of by-products such as THF and butanol. For this purpose, a nonacidic material, in the examples always magnesium silicate, is preferably used as support. The catalysts according to that invention achieves selectivities to GBL of over 90%; the selectivity to THF is generally reported as 2-10%.

All the types of catalyst described in the above-mentioned documents have the disadvantage that they produce a large amount of undesirable by-product or satisfactory activities can be achieved only for the preparation of GBL. In addition, Cr is frequently present in the catalyst.

It is an object of the present invention to provide a catalyst for the gas-phase hydrogenation of maleic acid and/or succinic acid and/or their above-mentioned derivatives which gives high selectivities to substituted or unsubstituted THF. This catalyst should, under appropriate reaction conditions, make it possible to obtain high yields of THF with at the same time formation of only small amounts of undesirable by-product. The catalyst should be free of Cr.

We have found that this object is achieved by a catalyst for the hydrogenation of $C_4$-dicarboxylic acids and/or derivatives thereof in the gas phase, which catalyst comprises a) 20-94% by weight of copper oxide (CuO), preferably 40-92% by weight of CuO, in particular 60-90% by weight of CuO, and b) 0.005-5% by weight, preferably 0.01-3% by weight, in particular 0.05-2% by weight, palladium and/or a palladium compound (calculated as metallic palladium) and c) 2-79.995% by weight, preferably 5-59.99% by weight, in particular 8-39.95% by weight, of an oxidic support selected from the group consisting of the oxides of Al, Si, Zn, La, Ce, the elements of groups IIIA to VIIIA and of groups IA and IIA of the Periodic Table of the Elements.

The catalysts of the present invention allow the hydrogenation of $C_4$-dicarboxylic acids and/or derivatives thereof in the gas phase to be carried out so that an unsubstituted or alkyl-substituted tetrahydrofuran is formed as main product in yields of significantly above 90%. It has surprisingly been found that the addition of palladium as active metal has a significant influence on the selectivity to THF.

For the purposes of the present invention, the groups of the Periodic Table of the Elements are designated according to the old IUPAC nomenclature.

For the purposes of the present patent application, the term $C_4$-dicarboxylic acids and derivatives thereof refers to maleic acid and succinic acid, which may each bear one or more $C_1$-$C_6$-alkyl substituents, and the anhydrides and esters of these unsubstituted or alkyl-substituted acids. An example of such an acid is citraconic acid. Preference is given to using MA. The THF produced can, depending on the starting material used, also bear one or more alkyl substituents.

The catalysts of the present invention comprise copper oxide which is known per se, palladium and/or a palladium compound, preferably palladium oxide and/or palladium nitrate, and an oxidic support having acid centers. It is preferred that no Cr is present in the catalyst. The catalysts can be used as shaped bodies, for example as rod extrudates, ribbed extrudates, other extrudate shapes, pellets, rings, spheres and granules.

The support material can be made up of one or more of the oxides of elements from the group consisting of Al, Si, Zn, La, Ce, the elements of groups IIIA to VIIIA and of groups IA and IIA. The support preferably has an appropriate number of acid centers. Preference is given to using an oxide of elements selected from the group consisting of Al, Si, Ti, Zn, Zr and/or Ce. Al is particularly useful. The support is used in an amount of <80% by weight, based on the total catalyst. The amount of copper oxide is >20% by weight and the amount of palladium and/or palladium compound is <5% by weight.

The catalyst of the present invention preferably consists exclusively of copper oxide, palladium and/or a palladium compound and aluminum oxide, apart from the usual impurities known to those skilled in the art.

The catalysts of the present invention can further comprise auxiliaries in an amount of from 0 to 10% by weight. For the purposes of the present invention, auxiliaries are organic and inorganic materials which contribute to improved processing during catalyst production and/or to an increase in the mechanical strength of the shaped catalyst bodies. Such auxiliaries are known to those skilled in the art and include graphite, stearic acid, silica gel and copper powder.

The catalysts of the present invention are produced by methods known per se to those skilled in the art, for example by coprecipitation of all or at least two components, precipitation of the individual components with subsequent intimate mixing, for example by kneading or processing in a pan mill, impregnation of the oxidic support with the other components a) and b) in one or more steps. Furthermore, the catalysts of the present invention can be obtained by shaping a heterogeneous mixture of the components a), b) and c).

Preference is given to processes in which the copper oxide is obtained in finely divided form intimately mixed with the support material, particularly preferably precipitation reactions. The catalyst of the present invention can be produced, for example, by precipitation of the appropriate metal carbonates and/or hydroxides from aqueous solution, washing, drying and calcination. The metal carbonates or hydroxides are obtainable, for example, by dissolving the corresponding metal salts in water and adding a precipitant, preferably sodium carbonate solution. Metal salts used are, for example, nitrates, sulfates, chlorides, acetates or oxalates. After precipitation, the precipitate obtained is filtered off, washed, dried and, if desired, calcined. Palladium and/or the palladium compound can be precipitated simultaneously with the other components or can be added to the precipitation product at any stage in processing.

An active composition comprising component a) or components a) and b) which has been produced in this way can be applied to the support c) in a customary manner, for example by pan milling or kneading, if appropriate in the presence of a binder, adhesive or peptizing agent. It is also possible to use other known methods for mixing the support material c) with an active composition comprising the components a) and b). For example, the support material in the form of powder or shaped bodies can be intimately mixed, coated or impregnated with precursor substances of the active composition, for example the abovementioned nitrates, sulfates, chlorides, acetates or oxalates or hydroxides of the respective metals or corresponding solutions. This pretreated support is then subjected to heat treatment to produce the active composition.

However, the catalyst is particularly preferably produced by coprecipitation of the components a) and c) and subsequent impregnation of the corresponding material obtained after drying, or of the shaped body obtained after pressing this material, with an aqueous solution of a soluble palladium compound, in particular a palladium salt solution, for example a solution of the nitrate, acetate, acetylacetonate, propionate, tetraaminepalladium acetate or tetraaminepalladium nitrate, preferably palladium nitrate. The materials or shaped bodies impregnated with the palladium salt solution are subsequently dried, preferably at from 50 to 150° C., and, if desired calcined at from 150 to 800° C. Impregnation of a shaped body is preferred.

The catalyst is generally subjected to activation, in general a treatment with hydrogen, before use in the reaction. In this way, the active catalyst species is produced. This is achieved by partial reduction of the oxides present in the catalyst mixture to the elemental metal which is active in the catalytic reaction carried out according to the present invention.

The catalyst of the present invention has a satisfactory operating life. Should, the activity and/or selectivity of the catalyst nevertheless drop during the operating time, it can be regenerated by means of measures known to those skilled in the art. These include reductive treatment of the catalyst in a stream of hydrogen at elevated temperature. If appropriate, the reductive treatment can be preceded by an oxidative treatment. Here, a gas mixture comprising molecular oxygen, for example air, is passed through the catalyst bed at elevated temperature. It is also possible to wash the catalyst with a suitable solvent, for example methanol, THF or GBL, and subsequently to dry it by means of a gas stream.

The reaction can be carried out in reactors in which the catalyst is arranged as a fixed bed. Particular preference is given to shell-and-tube reactors which enable the heat liberated in the reaction to be removed in an advantageous manner. MA is vaporized and passed through the reactor together with a hydrogen-containing stream of gas. Preference is given to a mixture having a high hydrogen content.

In some cases, the addition of other gaseous components such as steam, hydrocarbons, for example methane, ethane or n-butane, or carbon monoxide has a favorable effect on the selectivity, activity or long-term stability.

The concentration of the MA is from 0.1 to 5% by volume, preferably from 0.2 to 2% by volume. In the case of significantly higher MA concentrations, MA condenses out in the reactor and coats the catalyst with a liquid film. Significantly lower concentrations than those indicated above are possible in principle, but these would reduce the space-time yield and make the process unnecessarily expensive. The reaction temperature is set to a value in the range from 150 to 400° C., preferably from 200 to 300° C. Higher temperatures promote the formation of by-products, while lower temperatures lead to an unnecessary drop in the activity of the catalyst. The pressure is set to a value in the range from 0.5 to 50 bar, preferably from 1 to 20 bar. The GHSV (gas hourly space velocity=volume flow of reaction gas at STP divided by the volume of catalyst bed) is set so that complete conversion of MA is achieved. This makes the work-up of the product mixture easier and saves recirculation of unreacted MA. The GHSV is from 10 to 50 000 $h^{-1}$, preferably from 100 to 10 000 $h^{-1}$. The product mixture can be separated by methods known to those skilled in the art. Preference is given to circulating at least part of the unreacted hydrogen and thus reusing it in the hydrogenation.

It has been found that the formation of the desired end products can be controlled by variation of the reaction parameters. These are, in particular pressure, temperature and GHSV. Thus, an increased, sometimes even exclusive, formation of THF is generally observed at high pressures and temperatures and low GHSV values. In contrast, low pressures and temperatures and high GHSV values lead to increased formation of GBL.

The invention is illustrated by the following examples.

COMPARATIVE EXAMPLE C1

Production of CuO/Al$_2$O$_3$ Catalyst Pellets 3 l of water are placed in a heatable precipitation vessel fitted with a stirrer and are heated to 80° C. A metal salt solution consisting of 1754 g of Cu(NO$_3$)$_2$*2.5H$_2$O and 2944 g of Al(NO$_3$)$_3$*9H$_2$O in 4000 ml of water are metered simultaneously with a 20% strength by weight solution of sodium carbonate into this precipitation vessel over a period of one hour while stirring. The amount of sodium carbonate metered in is selected so that a pH of 6 is established in the precipitation vessel. After all the metal salt solution has been added, further sodium carbonate solution is metered in until the pH in the precipitation vessel has reached 8, and the mixture is stirred at this pH for another 15 minutes. The total consumption of sodium carbonate solution is 11 kg. The suspension formed is filtered and the solid is washed with water until the washings no longer contain nitrates (<25 ppm). The filter cake is firstly dried at 120° C. and subsequently calcined at 600° C.

600 g of this material are intimately mixed with 18 g of graphite and tabletted to produce pellets having a diameter of 3 mm and a height of 3 mm.

EXAMPLE 2

Production of a CuO/PdO/Al$_2$O$_3$ Catalyst According to the Present Invention 550 g of the pellets from Example 1, which had a water uptake capacity of 0.33 cm$^3$/g, were uniformly sprayed in an impregnation drum with a solution of 2.76 g of Pd as palladium nitrate in 172 ml of water, dried at 100° C. and finally calcined at 350° C. for 2 hours.

COMPARATIVE EXAMPLE C3

Production of a CuO/PtO/Al$_2$O$_3$ Catalyst for Comparison:

550 g of the pellets from Example 1, which had a water uptake capacity of 0.33 cm$^3$/g, were uniformly sprayed in an impregnation drum with a solution of 2.76 g of Pt as platinum nitrate in 172 ml of water, dried at 100° C. and finally calcined at 350° C. for 2 hours.

COMPARATIVE EXAMPLE C4, EXAMPLE 5, COMPARATIVE EXAMPLE C6

Hydrogenation of Maleic Anhydride 100 ml of the catalyst pellets from Comparative Example C1 or Example 2 were in each case mixed with 100 ml of glass rings of the same size and placed in a tube reactor having an internal diameter of 27 mm. The temperature of the reactor was regulated by means of oil flowing around it, and the reaction gas was passed through the reactor from the top downwards. MA was pumped as a melt into a vaporizer operated at 200° C. where it was vaporized in a stream of water The MA/hydrogen mixture, which had an MA concentration of 1.2% by volume, was then passed through the reactor and preheated above the catalyst bed. Complete conversion of MA was obtained in all examples.

Before the MA/hydrogen mixture was fed into the reactor, the catalyst was subjected to a pretreatment with hydrogen. For this purpose, 200 standard l/h of nitrogen were firstly passed through the reactor under atmospheric pressure and the reactor was simultaneously heated to a temperature in the catalyst bed of 180° C. over a period of one hour. The nitrogen flow was then increased to 950 standard l/h and an additional 50 standard l/h of hydrogen was fed in. A slight temperature increase in the catalyst bed to about 250° C. at the hot spot was observed. The hot spot migrates through the reactor from the reactor inlet to the end of the reactor. After the temperature had dropped to 190° C. throughout the catalyst bed, the nitrogen flow was reduced to 900 standard l/h and the water flow was increased to 100 standard l/h. The nitrogen flow was gradually switched off and the hydrogen flow was gradually increased to 250 standard l/h.

To compare the activity of the catalysts, the GHSV was increased from 2500 to 6000 $h^{-1}$.

| Ex. No. | Cat. No. | T [° C.] | GHSV [1/h] | $S_{BA}$ [mol %] | $S_{GBL}$ [mol %] | $S_{THF}$ [mol %] | $S_{others}$ [mol %] | Space-time yield [g$_{THF}$/hl$_{cat.}$] |
|---|---|---|---|---|---|---|---|---|
| C4 | C1 | 250 | 2500 | 0 | 0 | 93 | 7 | 89 |
|  |  | 250 | 3000 | <1 | 13 | 83 | 7 | 95 |
|  |  | 250 | 6000 | 30 | 62 | 7 | 1 | 16 |
| 5 | 2 | 250 | 2500 | 0 | 0 | 89 | 11 | 85 |
|  |  | 250 | 3000 | 0 | 0 | 91 | 9 | 104 |
|  |  | 250 | 6000 | 0 | 0 | 93 | 7 | 212 |
| C6 | C3 | 250 | 2500 | 0 | 2 | 76 | 22 | 73 |
|  |  | 250 | 3000 | 10 | 71 | 15 | 4 | 17 |
|  |  | 250 | 6000 | 32 | 59 | 7 | 2 | 16 |

$S_{XXX}$ = selectivity to the respective product

As can be seen from the table, in the case of the Pd-free catalyst of Comparative Example 1, the maximum space-time yield of tetrahydrofuran is achieved at a GHSV of 3000 $h^{-1}$. The THF selectivity of 93% is achieved by the catalyst at a space-time yield of 89 g $_{THF}$/hl$_{catalyst}$.

In comparison thereto, the catalyst according to the invention from Example 2 achieves an increase in the space-time yield to 212 g $_{THF}$/h*l$_{catalyst}$ at the same tetrahydrofuran selectivity of 93%. The platinum-doped catalyst from Comparative Example 3, on the other hand, displays a poorer activity and selectivity to tetrahydrofuran compared to the undoped system.

We claim:

1. A catalyst for the hydrogenation of $C_4$-dicarboxylic acid and/or derivatives thereof, in the gas phase, wherein said catalyst consists of 40-92% by weight of copper oxide, 0.005-5% by weight of palladium and/or of a palladium compound and 2-59.99% by weight of aluminum oxide as support material having acid sites.

2. A catalyst as claimed in claim 1 wherein said palladium compound is palladium oxide and/or palladium nitrate.

3. A process for producing the catalyst as claimed in claim 1, comprising treating a catalyst which consists of copper oxide and aluminum oxide as support material with a solution of a soluble palladium compound, drying and, optionally, calcining to obtain said catalyst.

4. A catalyst as claimed in claim 1 which is useful for the hydrogenation of preferably maleics anhydride in the gas phase.

* * * * *

UNITED STATES PATENT AND TRADEMARK OFFICE
CERTIFICATE OF CORRECTION

PATENT NO.       : 7,307,040 B2
APPLICATION NO.  : 10/482645
DATED            : December 11, 2007
INVENTOR(S)      : Schlitter et al.

It is certified that error appears in the above-identified patent and that said Letters Patent is hereby corrected as shown below:

In Claim 4, col. 8, indicated line 12:
"maleics anhydride" should read --maleic anhydride--

Signed and Sealed this

Twenty-ninth Day of April, 2008

JON W. DUDAS
*Director of the United States Patent and Trademark Office*